US00PP08201P

United States Patent [19]

Moore

[11] Patent Number: Plant 8,201

[45] Date of Patent: Apr. 13, 1993

[54] FLORIBUNDA ROSE PLANT NAMED 'MORHOOP'

[75] Inventor: Ralph S. Moore, Visalia, Calif.

[73] Assignee: Sequoia Nursery, Visalia, Calif.

[21] Appl. No.: 812,434

[22] Filed: Dec. 23, 1991

[51] Int. Cl.[5] ..... A01H 5/00

[52] U.S. Cl. ..... Plt./22

[58] Field of Search ..... Plt./1, 2, 7.1, 8.1, Plt./11, 22, 23

*Primary Examiner*—Howard J. Locker

[57] ABSTRACT

This invention relates to a new and distinct variety of Floribunda rose plant primarily identified by flowers with white petals and pink to red borders and the abundance of bloom.

1 Drawing Sheet

The present invention relates to a new and distinct variety of hardy, dwarf, bush type rose plant of the Floribunda class; the variety being primarily characterized—as to novelty—by the white buds and flowers with edges bordered with shades of pink to red.

The variety is further characterized by:

An abundance of bloom, with flowers usually borne several to the stem in loose clusters.

Fragrance: little or none.

A plant which is vigorous, of rounded, upright shape with medium size, semi-glossy foliage with pointed leaflets, the flowers being of open or decorative form.

The plant, which has a normal height of 18–24 inches or more, can easily be maintained at lesser height by occasional trimming.

A plant which grows and blooms satisfactorily both in greenhouse and outdoors; is good for growing in large pot or other containers and provides excellent garden decoration, both as an individual specimen or massed in the landscape.

The present variety of Floribunda rose was originated by me at my nursery located at Visalia, Calif., under conditions of careful control and observation, as a selfed seedling ($F_2$) from a cross between Dortmund (climber - not patented) as the seed parent and an unnamed seedling (Fairy Moss (U.S. Plant Pat. No. 3,083)×un-named striped Floribunda) as the pollen parent.

Subsequent to origination of the variety I successfully asexually reproduced it at the same nursery, located as aforesaid, by budding as well as by cuttings; the reproductions having run true in all respects.

The color photograph illustrates the variety, including the foliage, buds and flowers.

Referring now specifically to the new and distinct variety of Floribunda rose plant, the following is a detailed description thereof in outline; all major color plate identifications being by reference to the British Colour Council Horticultural Colour Chart, except where common terms of color definition are employed.

Type: Hardy; dwarf; bushy; upright; seedling; greenhouse; outdoors; cut flowers; garden decoration; potted plant.

Class: Floribunda.

*Variety identification.*—Morhoop (Commercial synonym: Hula Hoop).

Flowers borne: Several together (5–10 or more) on slender wirey stems.

Quantity of bloom: Abundant both outside and in greenhouse.

Bud:

*Sepals.*—Permanent; spear-shaped; recurved.

*Peduncle.*—Medium; slender but sturdy; erect; medium to light green; with no prickles.

*Before calyx breaks.*—Size — small. Form; long pointed with several foliaceous apendages on surface of bud; with foliaceous parts extending beyond the tip of the bud equal to one-half or more of its length. Color — medium green.

*As calyx breaks.*—Color — near white, often tinted pinkish. Opening: opens well in all weather.

Bloom:

*Size when fully open.*—Medium, averaging about 60 mm to 70 mm (2½ to 3").

*Petalage.*—Semi-double, averaging about 18–20 petals, arranged regularly.

*Form.*—Open with petals rolled loosely outward. Open flowers show stamens.

Petals: Fairly thick; satiny on inside and on outside surface.

*Shape.*—Outside petals, broad lanceolate with rounded tip; intermediate — broad lanceolate with rounded tip; inside — lanceolate with rounded tip.

*Color.*—Newly opened flower from a plant grown in plastic greenhouse (September 1991), Visalia, Calif. Outside petal: Outside surface — white (to near white) with border of pink to light red color (near Tyrian Rose 24/2 — may be lighter or darker) and blending into white. Inside surface — similar color and border as outside surface. When fresh, open petal may have very narrow border, or line of darker color. Intermediate petal: Outside surface similar to outside petal. Inside surface similar to outside petal. Inner petal: Outside surface — same as intermediate petal; inside surface — same as intermediate petal. General color effect; buds and newly opened flowers — white, with contrasting pink to light red border (a ring or hoop effect). Note: Color can vary, slightly depending upon weather, time of year, light intensity, etc. Three days open — color — similar to newly opened flowers, but lighter color. Behavior — opens well in all weather. Spent petals drop off. Flower longevity (September 1991) — plant in pot 6–8 days or longer. Cut flowers at living room temperature 3–4 days.

Reproductive organs:

*Stamens.*—Arranged regularly about pistils.

*Filaments.*—Varying length, medium long, yellow.

*Anthers.*—Well formed; yellow.

*Pollen.*—Some.

*Pistils.*—Average number.

*Styles.*—Varying length — medium long; redish; bunched.

*Ovaries.*—All enclosed in calyx.

*Hips.*—Some.

*Seed.*—Few.

Foliage:

*Leaves.*—Compound of five (sometimes three) leaflets; medium size; leathery; semi-glossy.

*Leaflets.*—Shape: fairly broad, elliptical; apex acute; base rounded to acute. Serrated. Color: medium green; new growth — normal (medium) green. Rachis: medium strength; upper side may have few or no prickles or hairs; grooved; underside may have several thorns (1 to 3) and few tiny prickles or hairs. Stipules: medium to short length; medium width; short to medium length narrow points which turn out usually at about 45 degrees or more.

Growth:

*Habit.*—Dwarf; bushy; upright; much branched.

*Growth.*—Free; vigorous; internodes short.

*Canes.*—Medium; slender; sturdy.

*Main stems.*—Color: medium green.

*Thorns.*—Several, medium to long, inclined downward. Prickles — none. Hairs — none.

*Branches.*—Color: medium green. Thorns: several; slender; medium to long — inclined downward. Prickles: none. Hairs — none.

The floribunda rose plant and its flowers as herein described may vary in slight detail due to climate, soil and cultural conditions under which the variety may be grown; the present description being of the variety as grown at Visalia, Calif.

The following is claimed:

1. A new and distinct variety of Floribunda rose plant of hardy, dwarf, bushy, upright, much branched habit, substantially as illustrated and described, characterized by slender buds and flowers of unique color pattern, essentially white edged or bordered with pink to medium red, and further characterized by the plant being of compact well rounded shape, vigorous, with the main stems and shoots being moderately thorny, said plant being easy to propagate from cuttings or by budding, with an abundance of medium semi-glossy foliage and an abundance of flowers borne several to the stem in loose clusters.

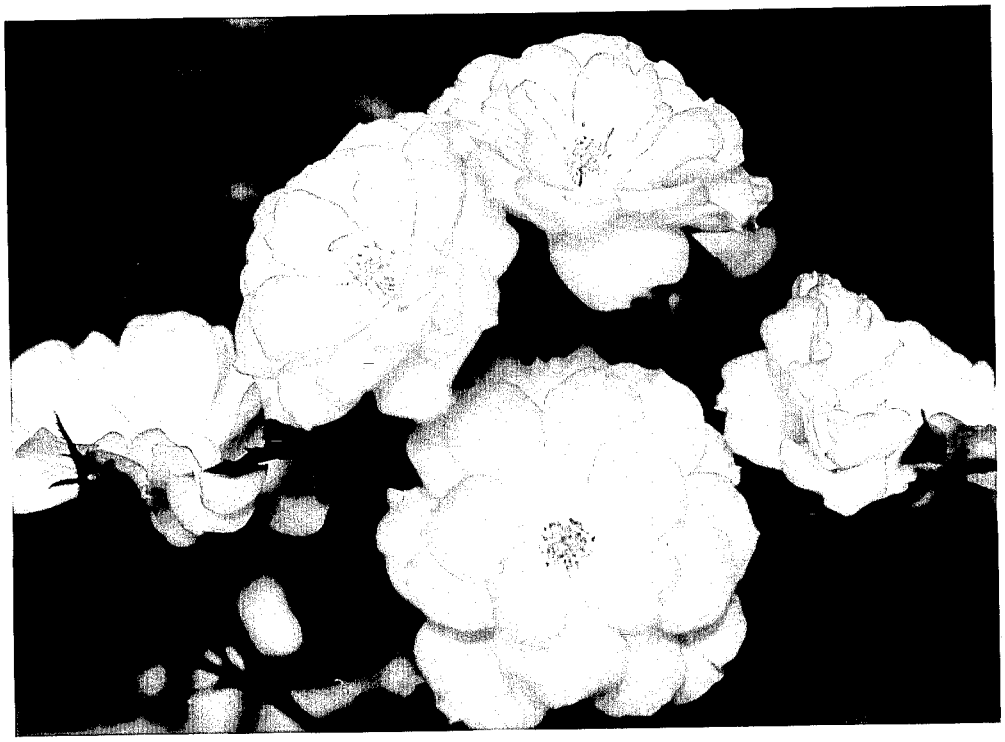

* * * * *